(12) United States Patent
Foreman et al.

(10) Patent No.: US 9,533,065 B2
(45) Date of Patent: Jan. 3, 2017

(54) AUTOMATED STERILIZATION PROCESS INTEGRATED WITH A BLOW FILL SEAL MACHINE

(71) Applicant: R.P. Scherer Technologies, LLC, Las Vegas, NV (US)

(72) Inventors: James Michael Foreman, Crystal Lake, IL (US); Arthur Baran, Bloomingdale, IL (US); Muhammad Amir, Huntley, IL (US)

(73) Assignee: R.P. Scherer Technologies, LLC, Las Vegas, NV (US)

( * ) Notice: Subject to any disclaimer, the term of this patent is extended or adjusted under 35 U.S.C. 154(b) by 0 days.

(21) Appl. No.: 14/656,858

(22) Filed: Mar. 13, 2015

(65) Prior Publication Data

US 2015/0182653 A1     Jul. 2, 2015

Related U.S. Application Data

(63) Continuation of application No. 13/902,385, filed on May 24, 2013, now Pat. No. 9,034,249.

(51) Int. Cl.
*A61L 2/24*     (2006.01)
*A61L 2/20*     (2006.01)
(Continued)

(52) U.S. Cl.
CPC .. *A61L 2/24* (2013.01); *A61L 2/07* (2013.01); *A61L 2/18* (2013.01); *A61L 2/20* (2013.01); *B65B 3/022* (2013.01); *B65B 2210/08* (2013.01)

(58) Field of Classification Search
CPC ........................................................ A61L 2/24
(Continued)

(56) References Cited

U.S. PATENT DOCUMENTS 4,790,117 A     12/1988   Hansen
4,979,347 A     12/1990   Shibauchi et al.
(Continued)

FOREIGN PATENT DOCUMENTS

EP     2495087 A1     9/2012
GB     1201069 A      8/1970

OTHER PUBLICATIONS

Forcinio, H., "BFS Equipment Streamlines The Package Process," Pharmaceutical Technology, 2010, vol. 34, pp. 38-45.
(Continued)

*Primary Examiner* — Sean E Conley
(74) *Attorney, Agent, or Firm* — Mendelsohn Dunleavy, P.C.

(57) ABSTRACT

A process and system for sterilization of a product pathway of a blow-fill-seal machine. The process comprises steps of: (1) isolating a holding tank from the product pathway; (2) supplying a sterilizing agent to the product pathway of the BFS machine when the holding tank is isolated; (3) stopping the supply of sterilizing agent to the product pathway when a threshold is reached; and (4) supplying filtered compressed air to the product pathway when the supply of sterilizing agent is stopped. The process is preferably executed automatically without human intervention once initiated. Also described is a system for carrying out the process including a processor, valves and temperature and/or pressure sensors which provide information to the processor to determine when to open and close the valves to supply sterilizing agent and/or compressed air to the product pathway or holding tank.

15 Claims, 2 Drawing Sheets

(51) Int. Cl.
  *B65B 3/02* (2006.01)
  *A61L 2/07* (2006.01)
  *A61L 2/18* (2006.01)

(58) Field of Classification Search
  USPC .......................................................... 422/114
  See application file for complete search history.

(56) References Cited

U.S. PATENT DOCUMENTS

| | | |
|---|---|---|
| 4,989,649 A | 2/1991 | Weiler et al. |
| 5,636,763 A | 6/1997 | Furness |
| 5,921,430 A | 7/1999 | Hansen et al. |
| 5,979,514 A * | 11/1999 | Andersson et al. ............ 141/91 |
| 6,298,638 B1 | 10/2001 | Bettle |
| 6,397,905 B1 | 6/2002 | Mayer et al. |
| 6,638,476 B1 | 10/2003 | Elias et al. |
| 7,038,219 B2 | 5/2006 | Clark et al. |
| 2005/0019239 A1 | 1/2005 | Bowen |
| 2006/0032189 A1 | 2/2006 | Giacobbe |
| 2010/0300043 A1 | 12/2010 | Thomasset |
| 2011/0085938 A1 | 4/2011 | Carbone et al. |
| 2011/0146202 A1 | 6/2011 | Imatani et al. |
| 2012/0118799 A1 | 5/2012 | Bowen |

OTHER PUBLICATIONS

Written Opinion and ISR issued Sep. 18, 2014 in corresponding PCT Application No. PCT/US2014/038183.
Complete File History for U.S. Appl. No. 13/902,385 as retrieved on May 28, 2015.

* cited by examiner

ABSTRACT# AUTOMATED STERILIZATION PROCESS INTEGRATED WITH A BLOW FILL SEAL MACHINE

CROSS-REFERENCE TO RELATED APPLICATIONS

This application is a continuation of U.S. patent application Ser. No. 13/902,385 filed May 24, 2013, the entire disclosure of which is herein incorporated by reference in its entirety.

BACKGROUND OF THE INVENTION

1. Field of the Invention

The present invention relates generally to sterilization carried out in a blow fill seal machine. In particular, the invention is directed to an automated sterilization process for the product pathway of a blow fill seal machine.

2. Description of the Related Technology

Blow-fill-seal (BFS) machines combine a process of antiseptically blow-molding hollow containers with an aseptic process of filling and sealing the containers, all in one machine cycle. By eliminating individual machines for separately blow-molding the container, filling the container, and sealing the filled container, the BFS machine delivers significant savings in space and efficiency while maintaining a medically sterile environment within the machines for the aseptic production process. Using the BFS technology, a container is formed, filled, and sealed in a continuous flow without human intervention, in a sterile enclosed area inside a machine, which ensures that the packaged product is free of contamination.

Over the last 20 years, BFS technology has become particularly prevalent within the pharmaceutical industry. It is now widely considered to be the superior form of aseptic processing technology for packaging of pharmaceutical and healthcare products by various regulatory agencies including the U.S. Food and Drug Administration (FDA).

The FDA emphasizes on product safety and requires manufacturers to ensure aseptic processing of all pharmaceuticals. It is thus critical to maintain a fully sterile environment within BFS machines, especially their product pathways. In a typical pharmaceutical packaging process, bulk pharmaceutical (solutions or liquids) prepared under low bio-burden or sterile conditions are delivered to the BFS machine in a sterile bulk holding tank, from which the pharmaceutical is delivered via a product pathway to a filling nozzle to be injected into formed containers.

Many processes for sterilizing BFS machines and/or their product pathways have been developed with various degrees of success. US 2011/0146202 discloses a process for maintaining a sterilization state in a mold-fill-seal machine. The internal space and outer surfaces of internal components of the machine are sterilized with a chemical liquid. Further, a positive-pressure environment is maintained within the machine with filtered clean air, which improves the aseptic level of packaged products. The outer surfaces of the machine may be sterilized with a chemical agent or heat-sterilized with aseptic water at high temperature. These treatments may be adjusted by consideration of the frequency of sterilization and the degree of contamination of the machine.

GB 1 201 069 discloses a process using steam to sterilize a BFS machine. The steam passes through pipes into a filling tank of the machine to sterilize the filling tank. The steam is used only for initial sterilization of the machine and is not suitable for sterilization of the BFS machine once its filling tank has been loaded with a product or when the BFS machine is in production mode.

U.S. Pat. No. 4,790,117 discloses a method of sterilizing the internal parts of a BFS machine by charging the machine with a sterilizing agent such as super-heated steam, a disinfection liquid, sterilizing gas, or the like for initial and continuous sterilization of the machine.

U.S. Pat. No. 6,298,638 discloses a process for maintaining sterility in a BFS machine during filling and minimizing the oxygen uptake of product being filled. The process requires placing the filling nozzle discharge port at a location that does not break a sterile fill plane which passes across the upper end of containers. This contributes to reducing the chance of contamination inside the containers.

Forcinio, "BFS equipment streamlines the package process," *Pharmaceutical Technology*, vol. 34, pp. 38-46, (2010) discloses the general concept of using steam to sterilize a product pathway in a BFS machine by an automated process. However, neither the critical process parameters nor other necessary details of the process are taught in the article.

The present invention provides a fully automated process and system for sterilizing a product pathway of a BFS machine that eliminates human manual intervention once the process has been initiated. Since human intervention may introduce errors and is a potential source of contamination to the BFS machine, the present process is a more reliable sterilization process.

SUMMARY OF THE INVENTION

In one aspect, the present invention is directed to a sterilization process for a product pathway of a BFS machine. The process includes the steps of: isolating a holding tank from the product pathway; supplying a sterilizing agent to the product pathway when the holding tank is isolated; stopping supply of the sterilizing agent to the product pathway when a threshold is reached; and supplying filtered compressed air to the product pathway when supply of the sterilizing agent is stopped, where the product pathway is a pathway a product travels from an outlet of the holding tank to a filling nozzle of the BFS machine and each said step of the process is controlled by a processor.

In another aspect, the present invention provides a sterilization process that monitors the temperature in the product pathway.

In yet another aspect, the present invention provides a sterilization process that monitors the pressure in the holding tank.

In yet another aspect, the present invention provides a sterilization process that further comprises a step of cleaning the product pathway by: retrieving the filters from the product pathway; supplying hot water to the product pathway; supplying the filtered compressed air to the product pathway; and reinstalling the filters to the product pathway.

In yet another aspect, the present invention provides a system for sterilizing a product pathway of a BFS machine, comprising a processor; a pressure sensor in a holding tank; a pressure sensor in the product pathway; and a temperature sensor in the product pathway, wherein the pressure sensors and temperature sensor are communicatively connected with the processor.

DETAILED DESCRIPTION OF THE PREFERRED EMBODIMENT(S)

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

In one aspect, the present invention relates to an automated sterilization process for sterilizing a product pathway of a blow-fill-seal machine. The process eliminates human intervention once the sterilization process is initiated, thus reducing the potential for error and the possibility of contamination.

The process of the present invention may be employed with any BFS machine that is integrated with a formulation system. The formulation system comprises a bulk holding tank (hereinafter "the holding tank") for temporary storage of product to be packaged. The formulation system also comprises a processor for controlling the operation of the BFS machine, which processor may optionally also control the sterilization process, or, optionally another processor may be provided for controlling the sterilization process.

Figure 2:
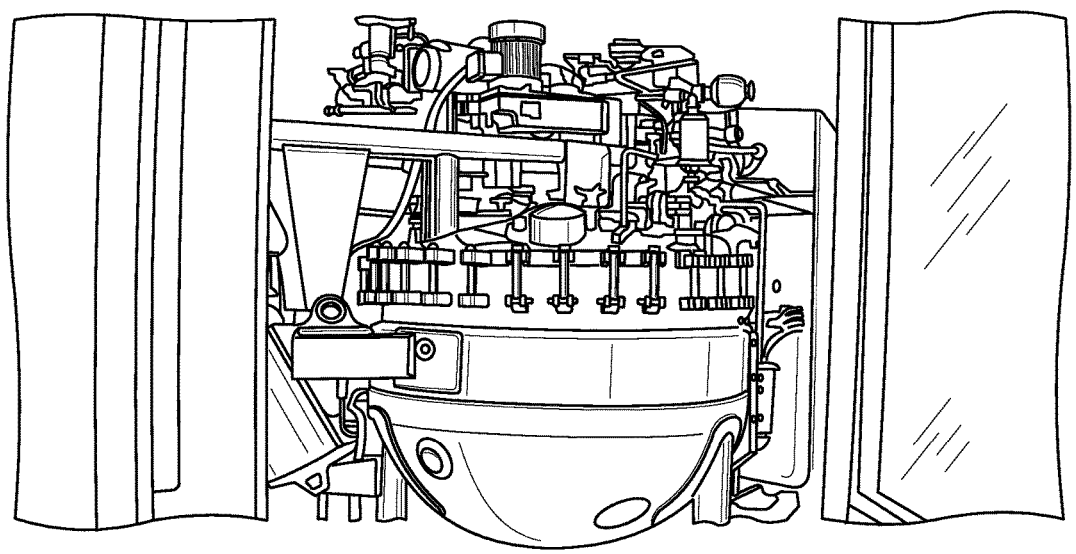
FIG. 2 depicts a formulation skid.
Figure 3:
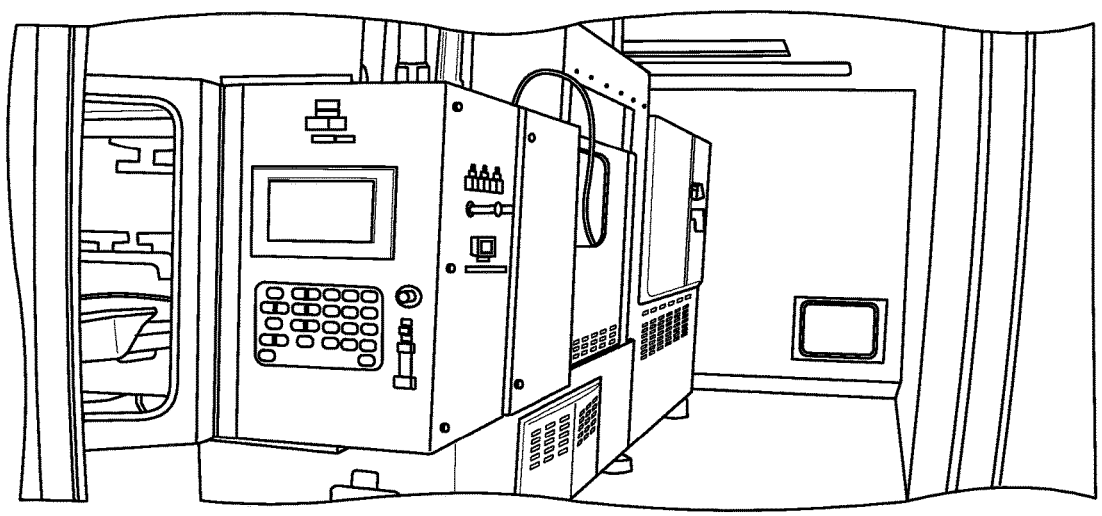
FIG. 3 depicts a blow-fill-seal machine.

There are plurality of conduits for supplying sterilizing agent (e.g., steam) and filtered compressed air to the BFS machine. Thus, the system is capable of directing sterilizing agent and filtered compressed air to the product pathway in the BFS machine. In one embodiment, the formulation system functions as a central controller of the sterilization process by using its processor(s) to issue commands to close or open valves, and monitor conditions of the process. In an exemplary embodiment, the formulation system is a formulation skid as shown in FIG. 2. The formulation skid may be integrated with a BFS machine shown in FIG. 3.

As used in the present application, the product pathway of a BFS machine is a conduit system through which a product travels from an outlet of a holding tank to a filling nozzle which injects the product into containers. In some embodiments, the product pathway comprises one or more conduits traveling from the outlet of the holding tank to a buffer tank, with further conduits connecting the buffer tank to the filling nozzle. The outlet of the holding tank has a product supply valve. Once the product supply valve is opened, the product in the holding tank is forced out of the holding tank, through the outlet and into the product pathway.

BFS machines are generally designed to carry out an aseptic process to make blow, fill and seal containers. It is thus important to keep the machine in a contamination-free state. BFS machines are usually kept in a sterile room, to reduce the potential for contamination. Among the various components of a BFS machine, the product pathway is a component that is likely to be contaminated during normal operation, because the machines need to be opened for retrieving the finished containers from the machine, which typically exposes the filling nozzle and internal surfaces of pipes and conduits upstream of the filling nozzle which form part of the product pathway the external environment. Therefore, the product pathway is at a high risk of being contaminated during normal operation of the BFS machine and requires periodic sterilization during the operation of the machine in order to maintain the required aseptic conditions.

To sterilize the product pathway, the present invention introduces one or more sterilizing agents selected from steam, ozone, hydrogen peroxide, hot water, or combinations thereof, into the product pathway. In some embodiments, steam is the sterilizing agent, and steam is used as an illustrative example in this application. A skilled person appreciates that the steam may be replaced by other sterilizing agents, with some routine adjustments to the sterilization process that is described in this application.

During normal operation of a BFS machine and before the sterilization process is initiated, filtered compressed air (hereinafter "compressed air") is supplied to the holding tank for maintaining a positive pressure in the holding tank. The compressed air may be air from the environment, which is first filtered by passing it through a high-efficiency particulate air (HEPA) filter or an ultra-low particulate air (ULPA) filter. The filtered air is compressed prior to feeding it to the holding tank. The same filtered compressed air may also be used for the sterilization process of the present invention.

The sterilization process is designed to be implemented as a processor-controlled, fully automated process. The various steps of the sterilization process involve automatically opening and closing valves as directed by the processor. No human intervention is needed once the sterilization process has been initiated. In one embodiment, an operator initiates the sterilization process by giving a command to the processor, for example, by pushing a button operatively linked to the system. Thereafter, the sterilization process is automatically carried out under the direction of the processor which issues commands to automatically open/close specific valves in a certain sequence. In an exemplary embodiment, a confirmation signal may optionally be required to initiate the sterilization process in order to reduce the chance of inadvertent initialization. The confirmation signal can be provided via a separate button, or other suitable means.

Figure 1:
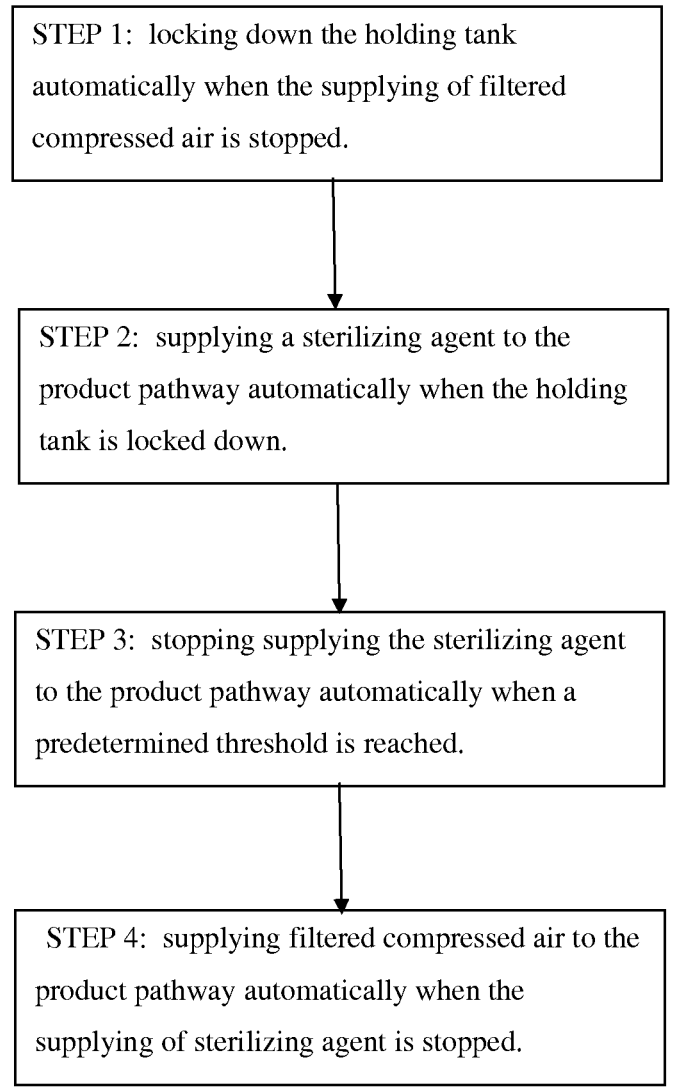
FIG. 1 is flow chart show a process for sterilizing a product pathway of a blow-fill-seal machine according to one embodiment of the present invention.

Referring to FIG. 1, the sterilization process of the present invention may be started, for example, by isolating a holding tank from the product pathway of the BFS machine. Specifically, at least one outlet from the holding tank to the product pathway is closed and preferably sealed by this step and maintained in a closed and pressurized state during the sterilization process.

In one embodiment, not all inlets of the holding tank are closed, e.g. at least one inlet for supplying compressed air to the holding tank is not closed. In this embodiment, the compressed air is continuously supplied to the holding tank during the sterilization process to ensure adequate positive pressure in the holding tank.

In another embodiment, the holding tank is locked down in the isolating step, which means that all the inlets and outlets of the holding tank are closed and sealed during the sterilization process. Locking down of the holding tank thus typically includes shutting off all the valves in and out of the holding tank. The purposes of this isolating step are to prevent flow of product from the holding tank to the BFS machine during the sterilization process, maintain a positive pressure in the holding tank, and prevent sterilization agents from flowing into the holding tank.

In a specific embodiment, once the operator initiates the sterilization process, the processor issues one or more commands to close the product supplying valve and stop supply of product from the holding tank to the product pathway. Once the holding tank is isolated from the product pathway, sterilization agent is ready to be supplied to the product pathway to sterilize the product pathway.

Isolation of the holding tank ensures that a positive pressure is maintained in the holding tank. In the isolating step, the processor sends at least one command to close one or more valves to separate the holding tank from the product pathway. In some embodiments, the isolated holding tank is locked down and is thus isolated from the rest of the BFS machine. Isolation of the holding tank from the product pathway is to ensure that the product in the holding tank is completely separated from the sterilization process and thus cannot be accidentally contaminated during the sterilization process. The holding tank remains isolated from the product pathway throughout the sterilization process. In an exemplary embodiment, the holding tank remains in this isolated state until at least after step (4) of the sterilization process of FIG. 1 has been completed.

A pressure sensor may be located in the holding tank and communicatively connected to the processor. Information from the pressure sensor allows the processor to monitor the internal pressure of the holding tank. Maintaining positive pressure in the holding tank prevents accidental contamination of the holding tank by the sterilization process, because the positive pressure prevents substances, including germs and other contaminants, from entering into the holding tank during the sterilization process. Certain embodiments of the present invention continuously measure the pressure in the holding tank during the sterilization process to ensure that the required positive pressure is maintained. If the pressure in the holding tank falls below a pressure threshold, the sterilization process may be stopped to feed additional filtered compressed air to the holding tank to establish the required level of positive pressure. After the pressure in the holding tank has risen above the required level, the processor will issue a command to resume the sterilization process. Alternatively, an alarm may sound if the pressure in the holding tank falls below a threshold level and steps may be taken to address potential contamination of the contents of the holding tank, as necessary.

The positive pressure in the holding tank is preferably maintained at or above a required pressure level in a range of about 30 to about 55 psig, or about 35 to about 45 psig. In one embodiment, the positive pressure in the holding tank is maintained at about 45 psig. Any time during the sterilization process, if the positive pressure in the holding tank falls to or below a pressure threshold in a range from about 1 psig to about 10 psig, it may triggers a routine that includes aborting the sterilization process, and supplying compressed air to the holding tank to raise the positive pressure back to the required pressure level. Then the holding tank is isolated again as in step (1) of FIG. 1, and the sterilization process is resumed. In one embodiment, the pressure threshold is about 1 psig.

After the holding tank is isolated from the product pathway, the processor automatically starts step (2) of FIG. 1, which is supplying a sterilizing agent to the product pathway. The conduit system supplying the sterilizing agent to the product pathway may be entirely within the formulation system, or may comprise some components from the formulation system. The conduit system is connected to the product pathway through a valve at a point that may be located near the holding tank outlet. The processor sends a command to open the valve, which allows the sterilizing agent to enter the product pathway from the conduit system. The sterilizing agent passes through the entire product pathway from the inlet located near the holding tank outlet to the filling nozzle.

The sterilizing agent may be supplied from a separate tank employed for storing the sterilizing agent for feeding to the product pathway. Alternatively, the sterilizing agent may be generated or supplied on an as needed basis, by, for example, generation of steam prior to and/or during the sterilization process. In some embodiments when the BFS machine is not in production, e.g. for initial sterilization prior to the start of a production run, the sterilization process may start with the step of supplying sterilizing agent to the product pathway.

In some embodiments, the sterilizing agent is steam. A temperature sensor may be located in the conduit system that supplies steam to the product pathway. The processor is communicatively connected to the temperature sensor to monitor the temperature of the steam in the conduit system. The temperature of the steam may be adjusted according to the type of germs potentially in the product pathway and the expected level of contamination in the product pathway. The temperature of the steam may be in a range of from about 100° C. to about 150° C., or from about 110° C. to about 130° C. In one embodiment, the temperature of the steam is about 121.1° C.

A pressure sensor may also be located in the conduit system that supplies steam to the product pathway. The processor is communicatively connected to the pressure sensor in order to monitor the pressure of the steam in the conduit system. The pressure of the incoming steam, i.e. the steam before it enters the product pathway, may be in a range of about 20 psig to about 40 psig, or about 23 psig to about 38 psig, or from 25 psig to 35 psig. In an exemplary embodiment, the pressure of incoming steam is about 30 psig.

The steam used in the sterilization process is itself sterilized, since it is generated from boiling water and maintained at a high temperature. So, generally speaking, any germs in the steam are killed by the high temperature. In some embodiments, further steps may be taken to ensure sterility of the steam, as necessary. For example, the steam may be irradiated using conventional means for sterilization.

The sterilization agent is passed through the product pathway under pressure and thereby sterilizes the product pathway. The processor may determine whether the desired level of sterility in the product pathway has been achieved by relying on one or more of the following criteria: sterilization time, Fo value in the product pathway and/or temperature in the product pathway. Once the desired sterility is reached, the processor issues a command to stop the supply of sterilizing agent to the product pathway by closing the valve through which sterilizing agent enters the product pathway.

The first criterion that the processor may use to terminate the supply of sterilizing agent in step (2) of FIG. 1 is the period of time the sterilizing agent is supplied to the product pathway, i.e. sterilization time. The sterilization time may be from about 10 to about 50 minutes, or about 20 to about 40 minutes, or about 25 to about 35 minutes. In one embodiment, the sterilizing agent is steam and the sterilization time is 30 minutes. Once the sterilizing agent has been supplied to the product pathway for a predetermined sterilization time, the supply of sterilizing agent to the product pathway may be terminated.

The sterilization time criterion is particularly suitable for embodiments where the sterilizing agent is not steam because the temperature in the product pathway, or Fo value may not be suitable for embodiments which do not use high temperature as a sterilization means. For example, in embodiments where the sterilizing agent is hydrogen peroxide, the sterilizing agent is typically supplied to the product pathway for a predetermined time (sterilization time). The appropriate length of the sterilization time may be determined by a skilled person through routine tests of the sterilizing agent on the product pathway of the BFS machine. Furthermore, the length of the sterilization time is also dependent on the sterilizing agent.

The second criterion that the processor may use to terminate the supply of sterilizing agent step (2) of FIG. 1 is the temperature in the product pathway. A suitable sterilizing agent for embodiments using the product pathway temperature as a criterion for terminating the sterilization step is steam. At least one temperature sensor is located in the product pathway to measure the temperature in the product pathway. The processor of the present invention is communicatively connected with the one or more temperature sensors in the product pathway to allow the processor to monitor the temperature in the product pathway and terminate the supply of sterilizing agent when the desired temperature is reached.

In these embodiments, the temperature in the product pathway determines the progress of the sterilization process. When the temperature in the product pathway has risen to or above a predetermined temperature level, the desired level of sterility has been reached in the product pathway. The predetermined temperature level is preferably from in a range of from about 100° C. to about 150° C., or from about 110° C. to about 130° C.

During the sterilization process, the processor compares the measured temperature in the product pathway with the predetermined temperature level. When the measured temperature is at or above the predetermined temperature level, the processor issue a command to automatically close the valve to stop the supply of sterilizing agent to the product pathway.

The third criterion that the processor may use to terminate the supply of sterilizing agent in step (2) of FIG. 1 is the Fo value in the product pathway. In embodiments using this criterion, the sterilizing agent may be steam. The processor may use measured product pathway temperatures to calculate the Fo value. Fo is defined as:

$$F_O = \Delta t \sum 10^{\frac{T-Tb}{z}}$$

where:
Δt Measurement interval between consecutive measurements of T
T Heating temperature (temperature measured in the product pathway)
Tb 121° C. (for steam pasteurization)
Z Temperature unit of logarithmic sterilization capability changes (generally, 10° C. is used).

Fo indicates an equivalent amount of time, in minutes at 121° C., which has been delivered to a product pathway by the sterilization process. For the calculation of Fo, a z-value of 10° C. is usually assumed. The z-value is the slope of the thermal death time curve and may be expressed as the number of degrees required to bring about a tenfold change in the death rate. The Fo value varies according to fluctuations in heat applied to the product pathway.

In the embodiment where Fo value is used to determine whether the desired sterility level in the product pathway has been reached, the supply of sterilizing agent to the product pathway is terminated when the Fo value reaches a value in a range of from about 50 minutes to 70 minutes, or from about 55 minutes to about 65 minutes. In one embodiment, the supply of steam as the sterilizing agent, to the product pathway is automatically terminated when the Fo value reaches about 60 minutes.

Once a threshold amount of sterilizing agent has been provided to the product pathway or the desired degree of sterilization has been achieved based on the criteria described above, the supply of the sterilizing agent to the product pathway is discontinued by the system as in step (3) of FIG. 1.

Once the flow of sterilizing agent to the product pathway has been discontinued, filtered compressed air is supplied to the product pathway in order to pressurize the product pathway. Once the supply of sterilizing agent to the product pathway is stopped, the processor automatically starts step (4) of FIG. 1, supply of compressed air to the product pathway. This is step may be referred to as blow down of the product pathway, functions to remove residual sterilizing agent in the product pathway. For example, when the sterilizing agent is steam, some moisture and/or condensation may be left in the product pathway. The compressed air blow down clears this from the product pathway and prepares it for production.

The compressed air enters the product pathway through a valve near the holding tank outlet. As a result, the compressed air can blow through the entire product pathway and exit at or near the filling nozzle. In one embodiment, the valve through which the compressed air enters the product pathway may be the same valve through which the sterilizing agent enters the product pathway. In another embodiment, the compressed air and sterilizing agent use different valves to enter the product pathway.

The present invention may include a pressure sensor in a conduit that supplies the compressed air to the product pathway. The processor monitors the pressure of the compressed air in the conduit using input from the pressure sensor. The pressure of the compressed air in the conduit before entering the product pathway may be in a range of from about 20 psig to about 60 psig, or about 25 psig to about 55 psig, or about 30 psig to about 50 psig. In one embodiment, the pressure of the compressed air in the conduit is about 40 psig.

The present invention may use one or both of blow down time and the temperature in the product pathway to determine when the blow down is completed. Once the predetermined criterion is met, the processor sends a command to close the valve through which the compressed air enters the product pathway.

The blow down time is the period of time during which compressed air is supplied to the product pathway during step (4) of FIG. 1. In some embodiments, the length of the blow down time is used as the criterion for terminating step (4). Typically, the blow down may be conducted for a blow down time in a range of from about 20 minutes to 60 minutes, or from about 25 minutes to 50 minutes, or from about 30 minutes to 45 minutes. In one embodiment, the blow down is automatically terminated after about 40 minutes.

In some other embodiments, the blow down is terminated when the temperature in the product pathway reaches a predetermined level. The predetermined temperature level may be in the range of from about 35° C. to about 60° C., or about 40° C. to about 50° C., or about 40° C. to about 45° C. In one embodiment, the blow down is automatically terminated once the temperature in the product pathway reaches about 45° C.

In some embodiments, the present invention maintains a positive pressure in the product pathway during the blow down step, and optionally during the entire sterilization process. This may be done to prevent or minimize the possibility of incidental contamination. Thus, to achieve this, a positive pressure can be maintained when the compressed air is supplied to the product pathway. In some embodiments, the BFS machine may supply its own compressed sterile air to the product pathway to maintain a positive pressure in the product pathway.

The present invention may also employ a pressure sensor in the product pathway. This allows the processor to monitor the pressure in the product pathway using input obtained from the pressure sensor. In some embodiments, the pressure in the product pathway may be maintained in a range of about 1 psig to about 20 psig, or about 1 psig to about 15 psig, or about 1 psig to about 10 psig. In one embodiment, the upper boundary for the pressure in the product pathway is about 10 psig and the lower boundary for the pressure in the product pathway is about 1 psig.

To terminate the blow down process, the processor sends a signal to close the valve and stop supplying compressed air to the product pathway. The processor then automatically directs the compressed air to the holding tank. The valve for providing compressed air to the holding tank is opened and compressed air enters the holding tank. The isolation of the holding tank from the product pathway, which has been maintained during the entire sterilization process before this step, is then terminated. At this stage of the sterilization process, the BFS machine returns to a production state, the product supply valve of the holding tank opens and is thus ready for supplying the product from the holding tank to the product pathway for packaging product.

The present invention may further include a step of generating a sterilization report, after the blow down step is completed.

In some embodiments, there is an optional step between steps (1) and (2) of FIG. 1. This optional step is a product pathway cleaning step. In such embodiments, after isolation of the holding tank from the product pathway is completed, the processor automatically starts the product pathway cleaning step, which includes one or more of: (i) retrieving the filters from the product pathway; (ii) supplying hot water to the product pathway; (iii) supplying compressed air to the product pathway; and (iv) reinstalling the filters to the product pathway.

In some embodiments, there are one or more filter housings in the product pathway. Each filter housing may have one or more filters for filtering the product to be packaged. Before using hot water to clean the product pathway, the filters in the product pathway are removed to clear the way for the hot water.

After step (i) is completed, the step (ii) may be automatically initiated to supply hot water to the product pathway. The hot water enters the product pathway through a valve near the holding tank outlet. The hot water flows through the product pathway at a flow rate of about 1 kg/min to about 10 kg/min, or about 2 kg/min to about 8 kg/min; or about 3.5 kg/min to about 6.5 kg/min. In one embodiment, the flow rate for the hot water in the product pathway is about 5.0 kg/min. In this step, hot water may be passed through the product pathway for a predetermined period of time, generally in a range of from about 2 minutes to about 15 minutes, or from 2 minutes to about 10 minutes, or from 4 minutes to about 6 minutes. In one embodiment, hot water flows through the product pathway for about 5 minutes. When the predetermined period of time is complete, the processor stops the supply of hot water to the product pathway by closing the hot water inlet valve.

After step (ii) is completed, step (iii) may be automatically initiated in order to supply compressed air to the product pathway. Step (iii) may be referred to as an air blow step. Compressed air, which may be the same compressed air used for step (4) of FIG. 1, is used in the air blow step. The air blow step may use compressed air with a pressure of from about 10 psig to about 30 psig, or from about 15 psig to about 25 psig. In one embodiment, the pressure of the compressed air in the air blow step is about 20 psig.

The air blow of step (iii) may be conducted for a predetermined period of time, which is generally in the range of from about 2 to about 10 minutes, or from 3 to about 8 minutes. In one embodiment, the air blow of step (iii) is conducted for about 5 minutes.

After step (iii) is completed, step (iv) may be automatically initiated in order to reinstall filters in the product pathway.

In one embodiment, the processor may be the same processor which forms part of the formulation system (e.g., formulation skid), and which communicates with the valves and temperature/pressure sensors of the present invention. The operator may initiate the product pathway sterilization process by some action such as pressing a button to send a signal to the processor to start the sterilization process. Thereafter, present invention eliminates manual valve manipulations throughout the entire sterilization process. All steps may be automatic, thereby reducing or eliminating the risk of human error and/or inadvertent contamination. As a result, the present invention provides the most robust level of sterility assurance and prevents the commercial/financial loss that results from contamination of otherwise sterile product in the event of a loss of positive pressure in the holding tank and product pathway.

The present invention is especially useful for producing aseptically packaged liquid products that cannot be sterilized by filtering prior to filling or at the point of filling. Conventionally, these products are bulk sterilized. However, there are several modes of failure in maintaining sterility from the time the bulk product is deemed sterile in the holding tank to the time the filling step is completed. For these types of products, maintaining a high level of sterility in the product pathway is particularly important in order to ensure an aseptic packaging process.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A system for sterilizing a product pathway of a blow-fill-seal machine, comprising:
    at least one processor;
    a pressure sensor in a holding tank that is configured to be isolated from the product pathway during sterilization by closing all inlets to and outlets from the holding tank;
    a pressure or temperature sensor in the product pathway;
    a valve for controlling supply of sterilizing agent to the product pathway;
    a valve for controlling supply of compressed air to the product pathway and/or the holding tank; and
    a processor that issues one or more commands to ensure that all inlets to and outlets from the holding tank are closed during the sterilization,
    wherein the pressure and temperature sensors communicate with the processor to provide pressure and/or temperature information to the processor and the processor determines when to open and close said valves based on said pressure and/or temperature information.

2. The system of claim 1, wherein the valve for controlling supply of compressed air is adapted to continuously supply compressed air to the holding tank.

3. The system of claim 1, wherein the sterilizing agent is selected from the group consisting of steam, ozone, hydrogen peroxide, hot water, and combinations thereof.

4. The system of claim 1, wherein the sterilizing agent is steam.

5. The system of claim 4, wherein the steam has a temperature in the range of from about 100° C. to about 150° C.

6. The system of claim 4, wherein the steam has a pressure in the range of from about 20 psig to about 40 psig.

7. The system of claim 4, wherein the valve for controlling the supply of sterilizing agent to the product pathway is adapted to stop supplying sterilizing agent to the product pathway when a threshold is reached.

8. The system of claim 7, wherein the threshold is a temperature in the product pathway.

9. The system of claim 8, wherein the threshold is a temperature in a range of from about 100° C. to about 150° C.

10. The system of claim 7, wherein the threshold is a period of time supplying the sterilizing agent to the product pathway.

11. The system of claim 10, wherein the period of time is in the range of from about 10 minutes to about 50 minutes.

12. The system of claim 7, wherein the threshold is the calculated Fo value.

13. The system of claim 12, wherein the Fo value is in the range of from about 50 minutes to about 70 minutes.

14. The system of claim 1, wherein the holding tank is adapted to have pressure raised by having filtered compressed air supplied at or above a threshold pressure.

15. The system of claim 14 wherein the threshold pressure is in a range of from about 1 psig to about 10 psig.

* * * * *